(12) United States Patent
McDermott

(10) Patent No.: US 6,248,336 B1
(45) Date of Patent: *Jun. 19, 2001

(54) COSMETIC MAKE-UP COMPOSITIONS

(75) Inventor: Padraig Hugh McDermott, Chatenay Malabry (FR)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/952,725

(22) PCT Filed: Apr. 23, 1996

(86) PCT No.: PCT/US96/05535

§ 371 Date: Nov. 20, 1997

§ 102(e) Date: Nov. 20, 1997

(87) PCT Pub. No.: WO96/36308

PCT Pub. Date: Nov. 21, 1996

(30) Foreign Application Priority Data

May 20, 1995 (GB) .................................................. 9510229

(51) Int. Cl.$^7$ ............................ A61K 7/021; A61K 7/06; A61K 7/11; A61K 7/075

(52) U.S. Cl. .......................... 424/401; 424/63; 424/70.7; 424/70.15; 424/70.19; 424/78.08; 514/937

(58) Field of Search ............... 424/78.08, 70.15, 424/401, 70.19, 70.7, 63; 514/937

(56) References Cited

U.S. PATENT DOCUMENTS

| | | | |
|---|---|---|---|
| 3,639,572 | 2/1972 | Heinrich et al. | 424/63 |
| 4,279,262 | 7/1981 | Horin et al. | 132/7 |
| 4,423,031 | 12/1983 | Murui et al. | 424/63 |
| 4,536,519 | 8/1985 | Suzuki et al. | 514/785 |
| 4,839,167 | 6/1989 | Yamamoto et al. | 424/71 |
| 4,917,883 | * 4/1990 | Strobridge | 424/59 |
| 5,041,281 | 8/1991 | Strobridge | 424/59 |
| 5,066,485 | 11/1991 | Brieva et al. | 424/63 |
| 5,143,722 | 9/1992 | Hollenberg et al. | 424/63 |
| 5,288,493 | * 2/1994 | Martino et al. | 424/401 |
| 5,356,627 | * 10/1994 | Da Cunha et al. | 424/401 |
| 5,389,363 | * 2/1995 | Snyder et al. | 424/70.7 |
| 5,393,526 | 2/1995 | Castro | 424/195.1 |
| 5,523,091 | 6/1996 | Pastour et al. | 424/401 |
| 5,609,852 | * 3/1997 | Galley et al. | 424/59 |
| 5,614,200 | * 3/1997 | Bartholomey et al. | 424/401 |
| 5,620,693 | * 4/1997 | Piot et al. | 424/401 |
| 5,688,493 | * 11/1997 | Sugawara et al. | 424/61 |
| 5,824,666 | * 10/1998 | Deckner et al. | 514/152 |
| 5,866,040 | * 2/1999 | Nakama et al. | 252/312 |
| 5,874,072 | * 2/1999 | Alwattari et al. | 424/70.7 |

FOREIGN PATENT DOCUMENTS

| | | |
|---|---|---|
| 0 530 084 A1 | 8/1992 | (EP) . |
| 0 545 002 A1 | 6/1993 | (EP) . |
| 0 568 035 A2 | 11/1993 | (EP) . |
| WO 93/14742 | 8/1993 | (WO) . |
| WO 94/17775 | 8/1994 | (WO) . |

* cited by examiner

Primary Examiner—Shelley A. Dodson
Assistant Examiner—Marina Lamm
(74) Attorney, Agent, or Firm—Dara M. Kendall; Fumiko Tsuneki; Michael E. Hilton

(57) ABSTRACT

A cosmetic make-up composition suitable for use as a mascara or the like and which is in the form of an emulsion comprising an insoluble polymeric material in an aqueous emulsion; and lipophilic oil components including a polyvinylpyrrolidone hexadecane copolymer. The compositions exhibit improved wear and water resistance and are removable with soap and water.

23 Claims, No Drawings

COSMETIC MAKE-UP COMPOSITIONS

TECHNICAL FIELD

The present invention relates to cosmetic make-up compositions, particularly eye make-ups and mascaras, comprising water-insoluble polymeric material in the form of an aqueous emulsion or latex. Said compositions have improved wear benefits compared to compositions known in the art and are easily removed with soap and water.

BACKGROUND OF THE INVENTION

Eye make-up compositions, including mascara, are significant products in the cosmetics market. Mascara enhances the beauty of the wearer by coating the eye lashes, or in some instances eyebrows, with color.

In spite of their beauty enhancing characteristics, conventional eye make-up preparations have been criticized for their failure to produce the desired effects during long periods of wear. Problems such as staining and smearing, commonly referred to as smudging, and flaking of the mascara from the eyelashes are well known. Even where longevity has been improved, such compositions also are known to be difficult to completely remove from the delicate eye area. An eye makeup composition conceptually having significantly superior wear life, yet, easy removability with soap and water would be very desirable.

Eye makeup compositions comprising polymeric emulsions in order to eliminate smudging are well known in the art and typically include water-insoluble polymers, also referred to as latexes. Such compositions including eye shadows as disclosed in U.S. Pat. No. 3,639,572, Henrich, issued Feb. 1, 1972; and mascaras as disclosed in U.S. Pat. No. 4,423,031, Murui et al., issued Dec. 27, 1983; and European Patent Application (EPA) 0568035, published Nov. 3, 1993. These compositions include plasticizers or solvents to assist in forming films using said latexes. These compositions are known to contain thickeners to adjust the viscosity of the composition. Said thickeners include water-soluble and water-swellable polymers, typically known for such use in the cosmetic art.

In a different embodiment of the above concept is disclosed in Patent Cooperation Treaty application WO 94/17775, published Aug. 18, 1994. The invention disclosed therein includes mascara compositions comprising water-based silicone elastomeric latex, emulsions as opposed to "water-based" acrylic polymers. Longer wear and durability is attributed to the used of the elastomeric latex as it is more compatible with the rest of the compositional matrix than the acrylic polymers.

Other compositions known in the art which seek to avoid the combination of plasticizers and insoluble-polymer are exemplified in EPO 0530084, published Mar. 3, 1993. This application discloses compositions comprising a dispersed phase and a dispersant phase, the dispersant phase containing at least one water-soluble polymer and the dispersed phase containing at least 50% wax. Said composition may contain other materials routinely used in cosmetic compositons including water-insoluble polymers.

Surprisingly, it has been found that the combination of water-insoluble polymeric materials in an aqueous emulsion and particular surfactants provides mascara and other cosmetic make-up compositions that have superior wear and are removable with soap and water. These make-up compositions can be fabricated in a multitude of forms, such as creams, pastes and solids. Preferably the compositions of the present invention are water-in-oil and oil-in-water emulsions.

SUMMARY OF THE INVENTION

According to one aspect of the present invention there is provided a cosmetic make-up composition suitable for use as a mascara or the like and which comprises:
(a) from about 0.1% to about 60% by weight of insoluble polymeric material in an aqueous emulsion;
(b) from about 0.1% to about 10% by weight of a first surfactant or mixture of surfactants having a weight averaged HLB of from about 3 to about 6; and
(c) from about 0.1% to about 10% by weight of a second surfactant or mixture of surfactants having a weight averaged HLB of from about 8 to about 15.

According to a second aspect of the present invention there is provided a cosmetic make-up composition suitable for use as a mascara or the like and which comprises:
(a) from about 0.1% to about 60% by weight of insoluble polymeric material in an aqueous emulsion; and
(b) from about 0.1% to about 10% by weight of an alkyl- or alkoxy-dimethicone copolyol having the general formula:

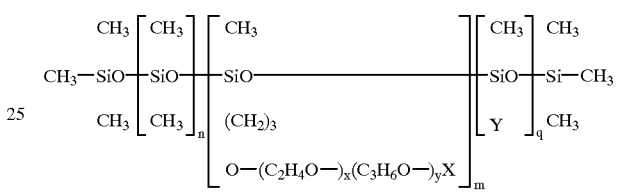

wherein X is a hydrogen atom or a $C_1$ to $C_{16}$ alkyl, alkoxy or acyl radical, Y is $C_8$–$C_{22}$ alkoxy or alkyl radical, n=from about 0 to about 200, m=from about 1 to about 40, q=from about 1 to about 100, the molecular weight of the residue $(C_2H_4O—)_x(C_3H_6O—)_yX$ being from about 250 to about 2000, x and y being selected so that the weight ratio of the oxyethylene/oxypropylene groups is from about 100:0 to about 20:80.

According to a third aspect of the present invention there is provided a cosmetic make-up composition suitable for use as a mascara or the like and which is in the form of an emulsion comprising:
(a) from about 0.1% to about 60% by weight of insoluble polymeric material in an aqueous emulsion; and
(b) from about 0.1% to about 80% by weight of lipophilic oil components including from about 0.1% to about 10% by weight of polyvinylpyrrolidone hexadecene copolymer.

The compositions of the invention exhibit improved wear, increased resistance to water and are easily removed with soap and water.

All percentages are by weight of composition unless otherwise indicated. All solutions are on a weight/weight concentration unless otherwise indicated.

DETAILED DESCRIPTION OF THE INVENTION

A first essential component of the make-up composition of the present invention is an insoluble polymeric material in an aqueous emulsion. Said materials, disclosed in the art as latexes, are aqueous emulsions or dispersions of polymeric materials comprising polymerized monomers, mixtures of monomers, derivatives of said monomers and mixtures of said monomers and mixtures thereof. These polymeric materials disclosed herein also include chemically modified (derivatives) of said polymeric material disclosed above. The polymerization process for making said polymeric material of the present invention is well known in the art. Such processes are disclosed in Kirk Othmer, *Encyclopedia* of *Chemical Technology*, Volume 14, "Latex Technology" 3rd Ed. 1981; incorporated herein by reference. These insoluble polymeric materials of the present invention comprise from about 0.1% to about 60%; preferably from about 2% to about 40% and most preferably from about 3% to about 30% by weight of the composition.

These insoluble polymeric materials comprise polymerized monomers, mixtures of monomers, derivatives of said monomers and mixtures of said monomers and mixtures thereof selected from the group consisting of aromatic vinyls, dienes, vinyl cyanides, vinyl halides, vinylidene halides, vinyl esters, olefins and their isomers, vinyl pyrrolidone, unsaturated carboxylic acids, alkyl esters of unsaturated carboxylic acids, hydroxy derivatives of alkyl esters of unsaturated carboxylic acids, amides of unsaturated carboxylic acids, amine derivatives of unsaturated carboxylic acids, glycidyl derivatives of alkyl esters of unsaturated carboxylic acids, olefinic diamines and isomers, aromatic diamines, terephthaloyl halides, olefinic polyols and mixtures thereof.

The insoluble polymeric material preferably comprise polymerized monomers, mixtures of monomers, derivatives of said monomers and mixtures of said monomers and mixtures thereof preferably selected from the group consisting of aromatic vinyls, dienes, vinyl esters, olefins and their isomers, unsaturated carboxylic acids, alkyl esters of unsaturated carboxylic acids, hydroxy derivatives of alkyl esters of unsaturated carboxylic acids, amides of unsaturated carboxylic acids and mixtures thereof.

In highly preferred embodiments the insoluble polymeric material comprise polymerized monomers, mixtures of monomers, derivatives of said monomers and mixtures of said monomers and mixtures thereof most preferably selected from the group consisting of aromatic vinyls, dienes, vinyl esters, alkyl esters of unsaturated carboxylic acids, hydroxy derivatives of alkyl esters of unsaturated carboxylic acids and mixtures thereof.

Specific polymeric material useful in the present invention include, but, are not necessarily limited to the Syntran Series (of latexes) from Interpolymer Corporation, for example Syntran 5170 and Syntran 5130 (acrylates copolymers formulated with added ammonia, propylene glycol, preservative and surfactant) and Syntran 5002 (styrenelacrylates/methacrylate copolymer formulated with added ammonia, propylene glycol, preservative and surfactant); the Primal Series (acrylic latexes) from Rohm & Hass; Appretan V (styrene/acrylic ester copolymer latexes) from Hoechst; Vinac (polyvinylacetate latex) from Air Products; UCAR latex resin 130 (polyvinylacetate latex) from Union Carbide; Rhodopas A Series (polyvinylacetate latexes) from Rhone Poulenc; Appretan MB, EM, TV (vinyl acetate/ethylene copolymer latexes) from Hoechst; 200 Series (styrene/butadiene copolymer latexes) from Dow Chemical; Rhodopas SB Series (styrene/butadiene copolymer latexes) from Rhone Poulenc; Witcobond (polyurethane latexes) from Witco; Hycar Series (butadiene/acrylonitrile copolymer latexes) from Goodrich; Chemigum Series (butadiene/acrylonitrile copolymer latexes) from Goodyear; and Neo Cryl (styrene/acrylates/acrylonitrile copolymer latex) from ICI Resins.

The make-up compositions of the present invention also preferably comprise from about 0.1% to about 10% by weight of a first surfactant or mixture of surfactants having an average HLB of from about 3 to about 6 and from about 0.1% to about 10% by weight of a second surfactant or mixture of surfactants having an weight average HLB of from about 8 to about 15.

Preferably the first surfactant comprises an alkyl- or alkoxy-dimethicone copolyol having the general formula:

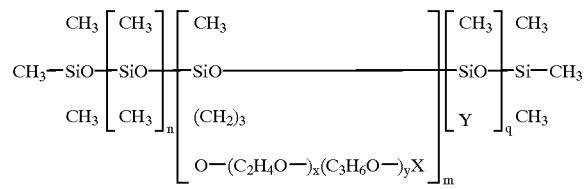

wherein X is a hydrogen atom or a $C_1$ to $C_{16}$ alkyl, alkoxy or acyl radical, Y is $C_8$–$C_{22}$ alkoxy or alkyl radical, n=from about 0 to about 200, m=from about 1 to about 40, q=from about 1 to about 100, the molecular weight of the residue $(C_2H_4O—)_x(C_3H_6O—)_yX$ being from about 250 to about 2000, x and y being selected so that the weight ratio of the oxyethylene/oxypropylene groups is from about 100:0 to about 20:80. Preferably Y is $C_{16}$–$C_{20}$ alkyl. Especially preferred herein in combination with the insoluble polymer emulsion from the viewpoint of increasing resistance to water is cetyl dimethicone copolyol. Hence according to a second aspect of the present invention there is provided a make-up composition comprising:
(a) from about 0.1% to about 60% by weight of insoluble polymeric material in an aqueous emulsion; and
(b) from about 0.1% to about 10% by weight of an alkyl- or alkoxy-dimethicone copolyol having the general formula:

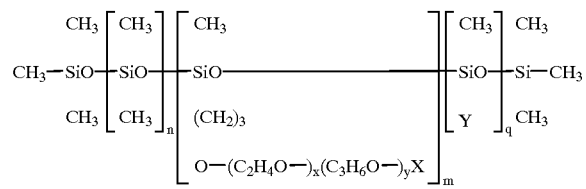

wherein X is a hydrogen atom or a $C_1$ to $C_{16}$ alkyl, alkoxy or acyl radical, Y is $C_8$–$C_{22}$ alkoxy or alkyl radical, n=from about 0 to about 200, m=from about 1 to about 40, q=from about 1 to about 100, the molecular weight of the residue $(C_2H_4O—)_x(C_3H_6O—)_yX$ being from about 250 to about 2000, x and y being selected so that the weight ratio of the oxyethylene/oxypropylene groups is from about 100:0 to about 20:80.

The second surfactant herein preferably comprises an organic base neutralized $C_{12}$–$C_{24}$ fatty acid. A preferred organic base herein is triethanolamine. A preferred fatty acid herein is stearic acid.

Preferably the compositions herein additionally comprise from about 0.1% to about 10% of polyvinylpyrrolidone hexadecene copolymer. This copolymer is useful in combination with the insoluble polymeric material in an aqueous emulsion and surfactants for improving water resistance and wear of the compositions. Hence according to a further aspect of the present invention there is provided a cosmetic make-up composition suitable for use as a mascara or the like and which is in the form of an emulsion comprising:
(a) from about 0.1% to about 60% by weight of insoluble polymeric material in an aqueous emulsion; and
(b) from about 0.1% to about 80% by weight of lipophilic oil components including from about 0.1% to about 10% by weight of polyvinylpyrrolidone hexadecene copolymer.

Optional ingredients useful in the present invention are selected based on either the various forms or attributes the composition is to have. The most preferred embodiments of the present invention are water-in-oil or oil-in-water emulsions. Some of the most common optional ingredients include oils and fats, emulsifiers, waxes, pigments and mixtures thereof.

A. Oils and Fats

Make-up compositions of the present invention can take the form of oil-in-water or water-in-oil emulsion compositions. These compositions are based on a combination of lipophilic materials optionally with one or more solvents. Said lipophilic materials typically comprise oils and fats generally known for use in the cosmetic art and are generally utilized herein in a level of from about 0% to about 70%, preferably from about 20% to about 60% by weight.

Oils typically used in cosmetics include those selected from the group consisting of polar oils, non-polar oils, volatile oils, non-volatile oils and mixtures thereof. These oils may be saturated or unsaturated, straight or branched chained, aliphatic or aromatic hydrocarbons. Preferred oils include non-polar volatile hydrocarbons including isodecane (such as Permethyl-99A®, available from Presperse Inc.) and the $C_7$–$C_8$ through $C_{12}$–$C_{15}$ isoparaffins (such as the Isopar® Series available from Exxon Chemicals).

Fats employed according to the invention are selected from the group consisting of fats derived from animals, vegetables, synthetically derived fats, and mixtures thereof wherein said fats have a melting point from about 55° C. to about 100° C. and a needle penetration, as measured according to the American standard ASTM D5, from about 3 to about 40 at 25° C. Preferably the fats selected for use in the present invention are fatty acid esters which are solids at room temperature and exhibit crystalline structure. Examples of fatty acid esters useful in the present invention include the glyceryl esters of higher fatty acids such as stearic and palmitic such as glyceryl monostearate, glyceryl distearate, glyceryl tristearate, palmitate esters of glycerol, $C_{18-36}$ triglycerides, glyceryl tribehenate and mixtures thereof.

B. Waxes

Waxes are defined as lower-melting organic mixtures or compounds of high molecular weight, solid at room temperature and generally similar in composition to fats and oils except that they contain no glycerides. Some are hydrocarbons, others are esters of fatty acids and alcohols. Waxes useful in the present invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 55° and 100° C. and a needle penetration, as measured according to the American standard ASTM D5, of 3 to 40 at 25° C. The principle of the measurement of the needle penetration according to the standards ASTM D5 consists in measuring the depth, expressed in tenths of a millimeter, to which a standard needle (weighing 2.5 g and placed in a needle holder weighing 47.5 g, i.e. a total of 50 g) penetrates when placed on the wax for 5 seconds.

The specific waxes useful in the present invention are selected from the group consisting of beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); $C_{24-45}$ alkyl methicones (silicone waxes); and mixtures thereof. Most preferred are beeswax, lanolin wax, carnauba, candelilla, ozokerite, ceresin, paraffins, microcrystalline waxes, polyethylene, $C_{24-45}$ alkyl methicones, and mixtures thereof.

C. Pigments

The solids component of the make-up compositions of the present invention contain cosmetically acceptable pigments selected from the group consisting of inorganic pigments, organic pigments, and pearlescent pigments. When employed, the pigments are present in proportions depending on the color and the intensity of the color which it is intended to produce. The level of pigments in the solid portion of the composition of present invention is from about 3% to about 30%, preferably from about 5% to about 20%. Pigments are selected from the group consisting of inorganic pigments, organic lake pigments, pearlesent pigments, and mixtures thereof. Said pigments may optionally be surface-treated within the scope of the present invention but are not limited to treatments such as silicones, perfluorinated compounds, lecithin, and amino acids.

Inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in the present invention include those selected from the group consisting of D&C Red No. 19 (CI 45,170), D&C Red No. 9 (CI 15,585),D&C Red NO. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

The pearlescent pigments useful in the present invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

D. Miscellaneous

In the present invention numerous optional ingredients may be added to provide additional benefits other than that attributed to the invention as defined above. For example, it is preferred that the composition of the present invention contain a preservative system to inhibit microbiological growth and maintain the integrity of the product. In the present invention, the preservative system does not have a detrimental effect on the composition.

Any optional ingredients known to those skilled in the art may also be used in the invention. Examples of optional ingredients are cosmetic fillers including, but not limited to, mica, talc, nylon, polyethylene, silica, polymethacrylate, kaolin, teflon; cosmetic preservatives including, but not limited to, methylparaben, propylparaben, butylparaben, ethylparaben, potassium sorbate, trisodium EDTA, phenoxyethanol, ethyl alcohol, diazolidinyl urea, imidazolidinyl urea, quaternium-15. Also, additives such as tall oil glycerides are easily incorporated into emulsion forms of the composition.

Water dispersible and oil dispersible clays may also be useful in the invention to thicken the water or the oil phase. The water dispersible clays comprise bentonite and hectorite, such as Bentone EW, LT from Rheox; magnesium aluminum silicate, such as Veegum from Vanderbilt Co.; attapulgite such as Attasorb or Pharamasorb from Engelhard, Inc.; laponite and montmorrilonite, such as Gelwhite from ECC America; and mixtures thereof. The oil dispersible clays comprise quaternium-18 bentonite, such as Bentone 34 and 38 from Rheox; the Claytone Series from ECC America; quaternium-18 hectorite, such as Bentone gels from Rheox; and mixtures thereof.

METHODS OF MANUFACTURE

The compositions of the invention can be prepared as follows.

1. Oil-in-Water Emulsion

The waxes and fats are placed in a vessel equipped with heating and mixing. The waxes and fats are heated to about 85° C. with low speed mixing until liquefied and homogeneous. At 85–90° C., pigments, any oil dispersible or soluble components are added. The mixing rate is increased to high and mixed until the pigments are uniformly dispersed throughout the lipid mixture; about 30–35 minutes. The emulsifiers are added to said lipid mixture while continuing to mix.

In a second vessel equipped with mixing and heating, the water and the remainder of the water dispersible components are added. The aqueous mixture is mixed with heating until this aqueous mixture is about 85° C. Q.S. for any water loss from said aqueous mixture.

The two mixtures are slowly combined and mixed with a high speed dispersator type mixer. The heat source is removed and the mixing is continued until the temperature of said combined mixture is from about 65° C.–70° C. Q.S. said combined mixture for any water loss. The preservatives and insoluble polymer component are added and mixed until homogeneous. Said combined mixture is cooled to about 45° C.–47° C. and any remaining components are added. Cooling and mixing is continued until said combined mixture is about 27° C. to about 30° C. Said combined mixture is transfered to suitable storage containers for subsequent filling of retail size packaging.

2. Water-in-Oil Emulsions (Examples I–V)

The components of phase A are premixed for 30 minutes at room temperature with high shear. The phase A premix is then heated to 85–90° C. with high shear. The wax phase B ingredients are premixed and heated to 90° C. with slow stirring for one hour. The wax phase is added to the phase A premix at 90° C. and mixed for 20 minutes with high shear. Cooling is commenced and the water phase ingredients are added. Mixing is continued with high shear. The mixture is cooled to 45° C. and the remaining ingredients are added. QS for paraffin loss.

EXAMPLES I–V

Water-In-Oil Emulsions

|   | I/% | II/% | III/% | IV/% | V/% |
|---|---|---|---|---|---|
| A. | | | | | |
| Petroleum Distillates | | | to 100 | | |
| Quaternium-18 Hectorite | 4 | 3.5 | 4.2 | 4.0 | 3.8 |
| Black Iron Oxide | 7.5 | 8.5 | 9.0 | 9.5 | 8.6 |

-continued

|   | I/% | II/% | III/% | IV/% | V/% |
|---|---|---|---|---|---|
| B. | | | | | |
| PVP/Hexadecene Copolymer | 1.7 | 2.5 | 2.2 | 1.9 | 2.0 |
| Polybutene | 1.9 | 2.75 | 2.0 | 2.5 | 1.8 |
| Beeswax | 2.8 | 3.5 | 4.4 | 4.0 | 3.0 |
| Carnauba wax | 2.5 | 4.4 | 3.5 | 3.3 | 4.0 |
| Paraffin wax | 1.5 | 2.2 | 2.0 | 2.5 | 1.8 |
| $C_{18}$-$C_{36}$ Acid triglycerides | 1.5 | 3.0 | 3.3 | 2.5 | 2.8 |
| Ethyl paraben | 0.15 | 0.15 | 0.15 | 0.15 | 0.15 |
| Methyl paraben | 0.2 | 0.2 | 0.2 | 0.2 | 0.2 |
| Propyl paraben | 0.2 | 0.2 | 0.2 | 0.2 | 0.2 |
| Zinc stearate | 2.5 | 2.0 | 2.1 | 2.3 | 1.9 |
| Cetyl dimethicone copolyol | 0.5 | 0.6 | 0.3 | 0.5 | 0.8 |
| Stearic acid | 0.9 | 1.0 | 1.8 | 1.9 | 1.5 |
| propylene glycol | 1.0 | 1.5 | 1.4 | 1.3 | 0.9 |
| propylene carbonate | 1.5 | 1.0 | 1.3 | 1.2 | 1.4 |
| C. | | | | | |
| Triethanolamine | 0.4 | 0.5 | 0.25 | 0.3 | 0.5 |
| Water | 2.5 | 2.65 | 1.4 | 1.8 | 2.0 |
| D. | | | | | |
| Ammonium Acrylate Copolymer[1] | 9.0 | 12.5 | 10.5 | 12.0 | 10.0 |
| E. | | | | | |
| Panthenol | 0.2 | 0.5 | 0.3 | 0.25 | 0.2 |
| Water | 1.0 | 1.0 | 1.5 | 0.8 | 1.2 |
| Quaternium-15 94% | 0.05 | 0.06 | 0.07 | 0.08 | 0.07 |
| Trisodium EDTA | 0.1 | 0.1 | 0.1 | 0.1 | 0.1 |
| F. | | | | | |
| phenoxyethanol | 0.8 | 1.0 | 0.75 | 1.1 | 0.85 |

[1]Syntran 5170, containing 41% by weight insoluble polymer solids, available from Interpolymer Corp.

What is claimed is:

1. A cosmetic make-up composition comprising:
   (a) from about 0.1% to about 60%, by weight of the composition, of an insoluble polymeric material in an aqueous emulsion;
   (b) from about 0.1% to about 10%, by weight of the composition, of polyvinylpyrrolidone hexadecene copolymer;
   (c) up to about 70%, by weight of the composition, of additional lipophilic components;
   (d) from about 0.1% to about 10%, by weight of the composition, of alkyl- or alkoxy-dimethicone copolyol surfactant having a weight average HLB of from about 3 to about 6;
   (e) from about 0.1% to about 10%, by weight of the composition, of organic base-neutralized $C_{12}$–$C_{24}$ fatty acid surfactant having a weight averaged HLB of from about 8 to about 15; and
   (f) from about 2.6 to about 3.65%, by weight of the composition, of added water.

2. A composition according to claim 1 wherein the insoluble polymeric material comprises polymerized monomers selected from the group consisting of aromatic vinyls, dienes, vinyl esters, olefins and their isomers, unsaturated carboxylic acids, alkyl esters of unsaturated carboxylic acids, hydroxy derivatives of alkyl esters of unsaturated carboxylic acids, amides of unsaturated carboxylic acids, derivatives of the foregoing monomers and mixtures thereof.

3. A composition according to claim 1 wherein the insoluble polymeric material comprises polymerized monomers selected from the group consisting of aromatic vinyls, dienes, vinyl esters, alkyl esters of unsaturated carboxylic acids, hydroxy derivatives of alkyl esters of unsaturated carboxylic acids, derivatives of the foregoing monomers and mixtures thereof.

4. A composition according to claim 1 comprising from about 2% to about 40%, by weight of the composition, of the insoluble polymeric material in an aqueous emulsion.

5. A composition according to claim 1 wherein the composition is in the form of a water-in-oil emulsion.

6. A cosmetic make-up composition comprising:
   (a) from about 0.1% to about 60%, by weight of the composition, of an insoluble polymeric material in an aqueous emulsion;
   (b) from about 0.1% to not greater than about 2.5%, by weight of the composition, of polyvinylpyrrolidone hexadecene copolymer;
   (c) up to about 70%, by weight of the composition, of additional lipophilic components;
   (d) from about 0.1% to about 10%, by weight of the composition, of alkyl- or alkoxy-dimethicone copolyol surfactant having a weight average HLB of from about 3 to about 6; and
   (e) from about 0.1% to about 10%, by weight of the composition, of organic base-neutralized $C_{12}$–$C_{24}$ fatty acid surfactant having a weight averaged HLB of from about 8 to about 15.

7. A composition according to claim 6 comprising from about 3% to about 30%, by weight of the composition, of the insoluble polymeric material in an aqueous emulsion.

8. A composition according to claim 6 wherein the composition is in the form of an oil-in-water emulsion.

9. A composition according to claim 6 wherein the insoluble polymeric material comprises polymerized monomers selected from the group consisting of aromatic vinyls, dienes, vinyl cyanides, vinyl halides, vinylidene halides, vinyl esters, olefins and their isomers, vinyl pyrrolidone, unsaturated carboxylic acids, alkyl esters of unsaturated carboxylic acids, hydroxy derivatives of alkyl esters of unsaturated carboxylic acids, amides of unsaturated carboxylic acids, amine derivatives of unsaturated carboxylic acids, glycidyl derivatives of alkyl esters of unsaturated carboxylic acids, olefinic diamines and isomers, aromatic diamines, terephthaloyl halides, olefinic polyols, derivatives of the foregoing monomers and mixtures thereof.

10. A composition according to claim 6 comprising from about 20% to 70%, by weight of the composition, of the additional lipophilic components.

11. A composition according to claim 6 comprising from about 20% to about 60%, by weight of the composition, of the additional lipophilic components.

12. A composition according to claim 10 wherein the additional lipophilic components comprise oil or fat.

13. A composition according to claim 12 wherein the oil is selected from the group consisting of polar oils, non-polar oils and mixtures thereof.

14. A composition according to claim 12 wherein the fat is selected from the group consisting of fats derived from animals, fats derived from vegetables, synthetically derived fats and mixtures thereof.

15. A composition according to claim 6 comprising from about 6.5% to about 10.5%, by weight of the composition, of wax.

16. A composition according to claim 15 comprising from about 6.8% to about 10.1%, by weight of the composition, of wax.

17. A composition according to claim 15 wherein the wax is selected from the group consisting of animal waxes, vegetable waxes, mineral waxes, hydrocarbon waxes, silicone waxes and mixtures thereof.

18. A composition according to claim 6 comprising from about 3% to about 30%, by weight of the composition, of pigment.

19. A composition according to claim 18 comprising from about 5% to about 20%, by weight of the composition, of pigment.

20. A composition according to claim 18 wherein the pigment is selected from the group consisting of organic lake pigments, pearlesent pigments and mixtures thereof.

21. A cosmetic make-up composition comprising:
   (a) from about 2% to about 40%, by weight of the composition, of an insoluble polymeric material in an aqueous emulsion, wherein the insoluble polymeric material comprises polymerized monomers selected from the group consisting of acrylate copolymer latexes, styrene/acrylate/methacrylate copolymer latexes, acrylic latexes, styrene/acrylic ester copolymer latexes, polyvinylacetate latexes, styrene/butadiene copolymer latexes, polyurethane latexes, butadiene/acrylonitrile copolymer latexes, styrene/acrylate/acrylonitrile copolymer latexes and mixtures thereof;
   (b) from about 0.1% to about 10%, by weight of the composition, of a polyvinylpyrrolidone hexadecene copolymer; and
   (c) up to about 70%, by weight of the composition, of additional lipophilic components;
   wherein the composition comprises from about 8.8 to about 10%, by weight of the composition, of total water; and
   wherein the composition is in the form of an emulsion and is a mascara or an eye make-up.

22. A composition according to claim 21 wherein the insoluble polymeric material is an acrylates copolymer formulated with added ammonia, propylene glycol, preservative and surfactant.

23. A composition according to claim 21 wherein the insoluble polymeric material in an aqueous emulsion comprises from about 3% to about 30%, by weight of the composition.

* * * * *